United States Patent [19]

McCulloch

[11] Patent Number: 5,217,006
[45] Date of Patent: Jun. 8, 1993

[54] IN OR RELATING TO A RESUSCITATOR

[76] Inventor: Norma D. McCulloch, 17 Broadsea Avenue, Ruby Bay, RD1, Upper Moutere, Nelson, New Zealand

[21] Appl. No.: 765,032

[22] Filed: Sep. 24, 1991

[51] Int. Cl.$^5$ .............................................. A62B 7/00
[52] U.S. Cl. ........................ 128/205.13; 128/205.17; 128/205.25; 128/205.24
[58] Field of Search ................... 128/205.13, 205.14, 128/205.15, 205.16, 205.17, 205.24, 205.25, 205.18, 202.28, 202.29, 203.28, 203.11

[56] References Cited

U.S. PATENT DOCUMENTS

| | | | |
|---|---|---|---|
| 2,007,330 | 7/1935 | Hicks | 128/203.28 |
| 2,428,451 | 10/1947 | Emerson | 128/205.18 X |
| 2,970,749 | 2/1961 | Montague | 128/205.13 X |
| 3,037,497 | 6/1962 | Roberson | 128/202.29 |
| 3,046,978 | 7/1962 | Lea | 128/205.13 |
| 3,099,985 | 8/1963 | Wilson et al. | 128/203.11 |
| 3,136,312 | 6/1964 | Gattone | 128/205.13 |
| 3,196,866 | 7/1965 | Adams | 128/205.13 |
| 3,796,216 | 3/1974 | Schwarz . | |
| 3,882,860 | 5/1975 | Frimberger | 128/205.13 X |
| 4,498,472 | 2/1985 | Tanaka | 128/203.28 X |
| 4,627,796 | 12/1986 | Moore . | |

FOREIGN PATENT DOCUMENTS

| | | | |
|---|---|---|---|
| 0252618 | 1/1988 | European Pat. Off. . | |
| 152864 | 11/1969 | New Zealand . | |
| 399657 | 3/1966 | Switzerland | 128/205.18 |
| 769347 | 3/1957 | United Kingdom . | |
| 841558 | 7/1960 | United Kingdom . | |
| 1030404 | 5/1966 | United Kingdom . | |
| 1157331 | 7/1969 | United Kingdom . | |
| 2141490 | 12/1984 | United Kingdom . | |
| 2145335 | 3/1985 | United Kingdom . | |
| 2182249 | 5/1987 | United Kingdom | 128/203.28 |

Primary Examiner—V. Millin
Assistant Examiner—Sebastiano Passaniti
Attorney, Agent, or Firm—Wenderoth, Lind & Ponack

[57] ABSTRACT

A manually operated resuscitator is provided. The resuscitator has an inner member provided in an outer member. The inner and outer members have an arrangement of apertures and valves to enable ambient air to be drawn into the pump in its non-pressurizing stroke and on a pressurizing stroke the inner member is capable of discharging air. The pump is connected to a mask by a rigid conduit. The face mask is positionable over the nose and mouth of a patient so as to form a fairly airtight seal with the face of the patient. An exhale aperture is provided adjacent the face mask which enables the patient to exhale air to the exterior of the device. The dimensions and configuration of the pump and conduit are suitable for human resuscitation purposes. Furthermore, the construction is such that the user of the device can hold the mask with one hand and the outer cylindrical member can be held and reciprocated by the other hand of the user so that when ambient air is pumped from the pump to the face mask, an increased pressure is applied to the mask so as to enhance the seal between the mask and the face of a patient.

10 Claims, 3 Drawing Sheets

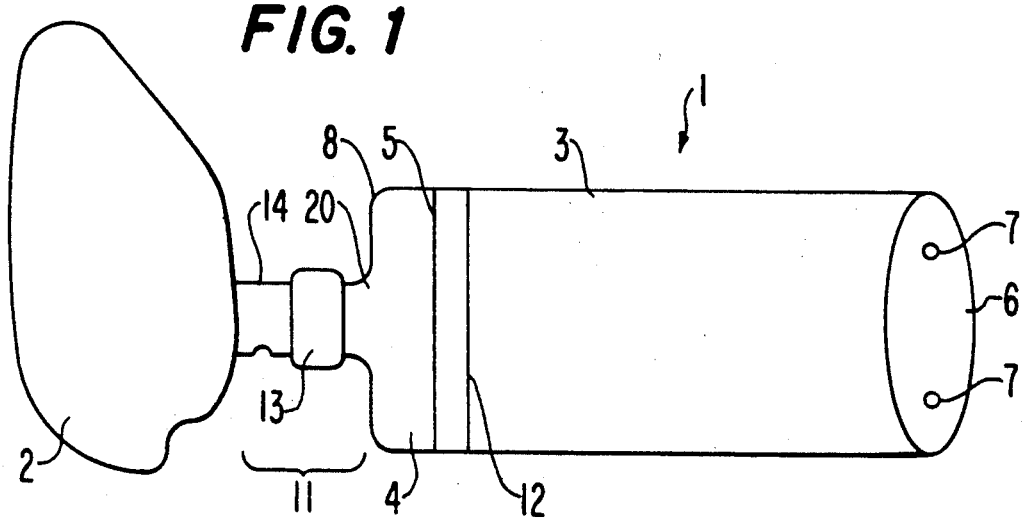
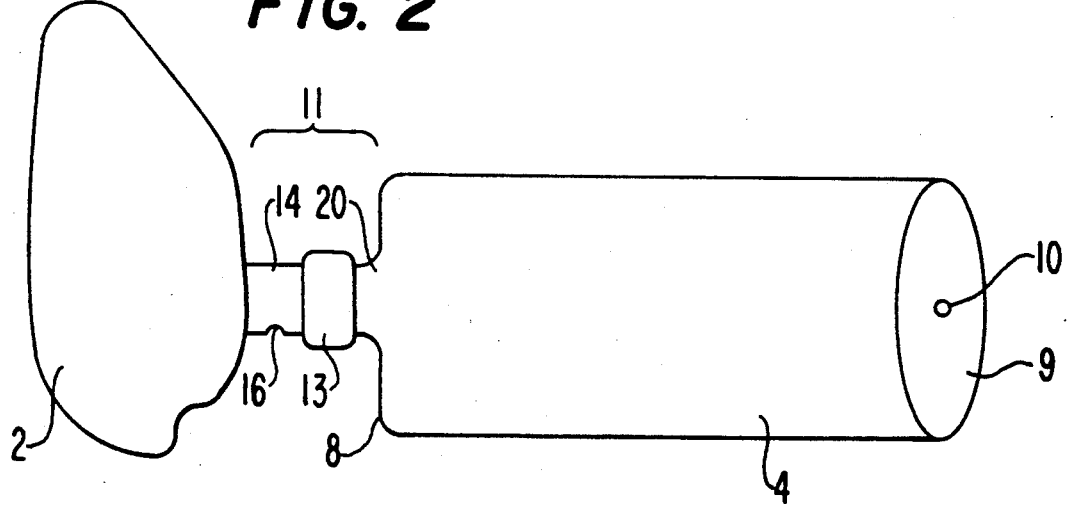

2

IN OR RELATING TO A RESUSCITATOR

BACKGROUND OF THE INVENTION

This invention relates to a manually operated resuscitator. Mouth-to-mouth resuscitation is a well known technique used to assist breathing of individuals in need. However, this is physically very exhausting for the administrator of the resuscitation and is also associated with the risk of either the administrator or recipient of the resuscitation transmitting infectious diseases.

U.S. Pat. No. 4,934,360 shows a manually operated resuscitator device. However, the construction of the device shown is fairly complicated and relies on adjacent bellows. Therefore, the device is not particularly compact.

U.S. Pat. No. 4,088,131 discloses a lung inflation system. However, the device relies on a manual compression bag. The device shown is also of a fairly complicated construction.

SUMMARY OF THE INVENTION

It is an object of the foregoing invention to provide a breathing apparatus which will go at least some way to overcoming the foregoing desiderata in a simple yet effective manner or which will at least provide the public with a useful choice.

Accordingly, the invention consists in a breathing apparatus comprising a manually operable telescopic pneumatic pump and a mask, the pump being in communication with the mask so that the output from the pump is passed to the mask.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

A preferred embodiment of the breathing apparatus will now be described with reference to the accompanying drawings in which:

FIG. 1 is a diagrammatic perspective view of the resuscitator according to one preferred form of the invention;

FIG. 2 is a diagrammatic perspective view of an inner member for use in the resuscitator according to the preferred form of the invention;

DETAILED DESCRIPTION OF THE INVENTION

Figure 3:
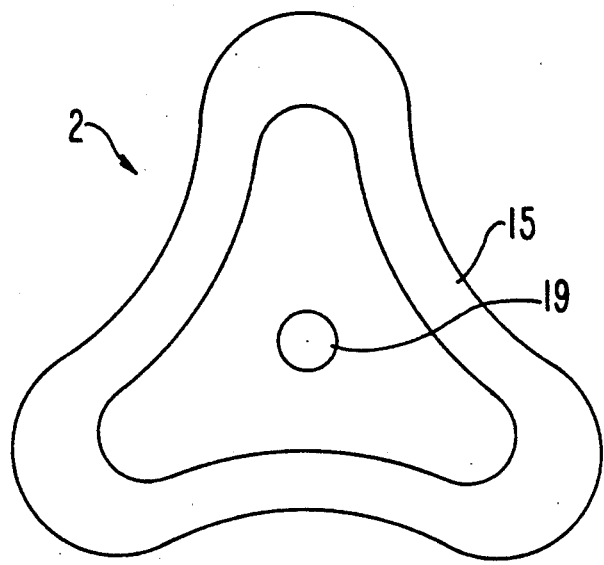
FIG. 3 is an end elevation of a mask for use in a resuscitator according to the preferred form of the invention.

A resuscitator is provided which comprises a manually operable telescopic pneumatic pump 1 in communication with a mask 2. In the preferred form the telescopic pump 1 comprises two substantially cylindrical members; an outer member 3 and inner member 4. The inner member 4 can be positioned into the open proximal end 5 of the outer member 3. The outer member 3 is able to slide over the inner member 4 but the fit between the inner member 4 and outer member 3 is substantially tight.

The inner member 4 preferably telescopes into the outer member 3 such that the distal end 9 of the inner member 4 is substantially adjacent to the distal end 6 of the outer member 3 when the pump 1 is in a closed configuration (as shown in FIG. 1).

The outer member 3 preferably comprises a hollow cylinder, open at the proximal end 5 and substantially enclosed at the distal end 6. One or more apertures 7 are provided in the distal end 6.

The inner member 4 comprises a hollow cylinder which is substantially enclosed at both proximal end 8 and distal end 9. An aperture 10 may be provided in the distal end 9 of the inner member 4. A tubular outlet 20 having an aperture therethrough may be provided at the proximal end 8. The outlet 20 may open into the inside of the inner member 4.

The inner member 4 may be substantially longer longitudinally than the outer member 3 as desired. In this embodiment, the proximal end 8 of the inner cylinder 4 extends substantially beyond that of the proximal end 5 of the outer cylinder 3. This exposes the proximal end 8 of the inner member 4 which may enhance ease of operation.

Preferably, the pump 1 is of large enough dimensions to expel a suitable amount of air into a person to inflate the person's lungs to a sufficient degree to aid resuscitation. However, the pump should be small enough to be hand operable. For example, the pump may have a volume sufficient to contain substantially 1000 mls of air. An axial line or marking 12 may be marked on the outer member 3. Thus, when the outer member 3 is drawn out in use so that the marking 12 aligns with the distal end 9 of the inner member 4, substantially 900 mls of air may be drawn into the pump 1. To this end, it is desirable for the outer member 3 to be formed from substantially transparent material so that the distal end 9 can be viewed therethrough.

Also, instructions may be marked on the outer member 3. The instructions may for example state that the outer member 3 should be drawn out to the required distance.

Further instructions for use of the apparatus may also be inscribed on the outer member 3, for example.

Figure 6:
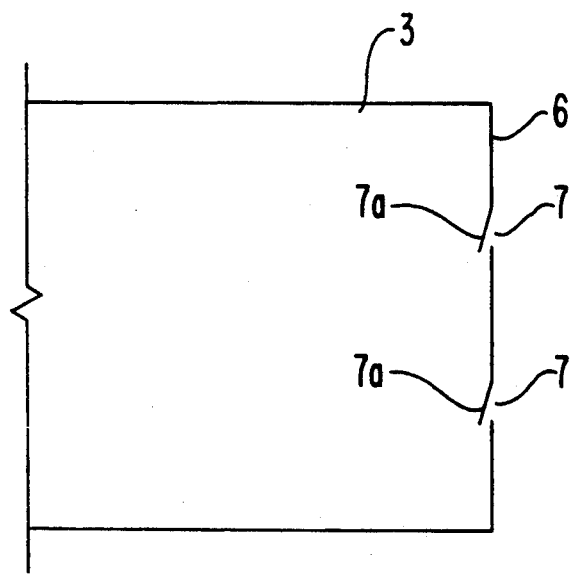
FIG. 6 is a schematic longitudinal section view taken along apertures in a distal end of the outer member of the pump according to the preferred form of the invention.

Preferably, valves 7a are positioned on the inside surface of the distal end 6 so as to cover the aperture or apertures 7 as shown in FIG. 6. The valves 7a are desirably flap valves but any suitable valve may be used within the scope of the invention. The flap valves 7a may for example be formed from suitably flexible material such as flexible plastic. In one embodiment the flap valves 7a may comprise circular material adhered to the inner surface of the distal end 6. The flap valves 7a should only be adhered over part of the surface thereof so that they are able to partly uncover the apertures 7 in use as required.

The valves 7a may be of a type such that when the inner member 4 is being forced into the outer member 3 the valves 7a covering the apertures 7 are closed. However, when the inner member 4 is drawn out of the outer member 3 a vacuum is created such that the valves covering the apertures 7 open thus allowing air to enter into the pump 1.

A mask 2 is provided which is in communication with the pump 1. The communication means between the mask 2 and pump 1 shall be termed a valve body assembly 11 herein. In the embodiment shown, the valve body assembly 11 comprises the tubular outlet 20, an expanded collar 13 and tubular connection 14. However, alternative embodiments are envisaged within the scope of the invention. The valve connection body 11 may for example comprise a single tubular component. Desirably, a bore 19 passes through the tubular connection 14, collar 13 and tubular outlet 20 such that air is able to pass into the mask 2 from the pump 1.

The mask 2 is of suitable dimensions such that it can be placed over the mouth, or nose, or nose and mouth of the recipient receiving resuscitation. The mask 2 may for example be substantially triangular when viewed from the end, as shown in FIG. 3. The mask 2 is desirably formed from substantially flexible material, such as plastic, with smooth or rounded edges 15 for comfort.

Figure 4:
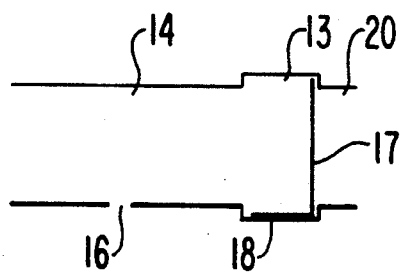
FIG. 4 is a sectional elevation of a connection between the mask and pump where the recipient of the resuscitation is exhaling air in use according to the preferred form of the invention.
Figure 5:
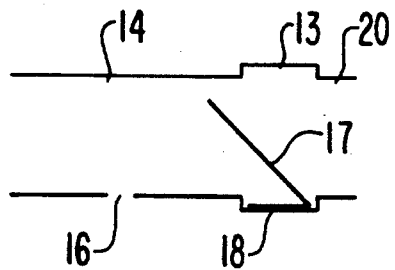
FIG. 5 is a sectional elevation of the connection device between the mask and pump where air is provided to the recipient of the resuscitation according to the preferred form of the invention.

A further valve 17 is provided to cover the bore 19. The valve 17 may for example consist of a flap valve but other suitable valves may also be employed. A flap valve 17 is shown in FIGS. 4 and 5. The flap valve 17 may for example comprise a circular member formed from substantially flexible material, such as plastic. The flap valve 17 may be attached along one edge thereof at 18 for example. The flap valve 17 may suitably be positioned so as to cover the bore 19 at tubular outlet 20 for example and therefore may be positioned substantially within the collar 13.

An aperture 16 is provided and this may conveniently be formed in the connection 14. This forms a vent which enables the recipient of the resuscitation to exhale air during use of the device.

Thus, when the pump 1 is supplying air to the recipient of the resuscitation as shown in FIG. 5, the flap valve 17 moves away from the entrance to the tubular outlet 20 so that air can be supplied to the mask 2 from the pump 1. When the recipient of the resuscition is exhaling air, the flap valve 17 closes (as shown in FIG. 4) and the expelled air is able to pass through the aperture 16.

When the recipient of the resuscitation is able to breath without assistance, the flap valve 17 closes and enables the recipient to breath normally via the aperture 16.

The breathing apparatus is preferably composed of light-weight yet durable materials such as plastic.

The preferred use of the invention according to one preferred form of resuscitator shall now be described.

The resuscitator is able to be used on a person requiring resuscitation. The device is manually operated by the administrator of the resuscitation. The device may be sterilized in a suitable sterilizing solution.

The mask 2 is positioned over the nose, mouth, or both nose and mouth of the recipient of the resuscitation. The outer member 3 is drawn back from the position shown in FIG. 1 to a position wherein the marking 12 is aligned with the distal end 9 of the inner member 4. The outer member 3 is then forced towards the mask 2 so that air is forced into the interior of the mask and thus to the recipient's lungs. When the recipient exhales air the flap valve 17 closes and the exhaled air exits through the aperture 16. The pumping procedure described above should be carried out every 5 seconds for example so that the chest of the recipient rises and falls. When the recipient recovers, the aperture 16 allows the recipient to breathe unassisted.

In case of heart failure, the pumping procedure may be carried out twice followed by 15 heart compressions for example. This procedure should be repeated as required.

Thus it can be seen that at least in its preferred form a hand operated breathing device is provided which is readily transportable and compact. The device is able to be used easily and effectively for providing air to people in need of resuscitation. The pump shown is easily operated and requires little strength on behalf of the operator. The device enables people to be resuscitated without the requirement of mouth-to-mouth resuscitation, therefore reducing the risk of spreading infectious diseases.

What is claimed is:

1. A manually operable resuscitation device comprising:
    a pneumatic pump including a rigid inner cylindrical member, a rigid outer cylindrical member telescopically and slidably mounted over said inner cylindrical member, said inner member having an air outlet at an end thereof which projects outwardly of said outer cylindrical member when said outer cylindrical member is slidably mounted over said inner cylindrical member, and valve means for allowing ambient air to be drawn into said pump during a non-pressurizing stroke in which said outer cylindrical member is partially and telescopically slid outwardly over said inner cylindrical member in a direction away from said air outlet and for causing air to be discharged through said air outlet of said inner cylindrical member during a pressurizing stroke in which said outer cylindrical member is telescopically slid inwardly over said inner cylindrical member in a direction towards said air outlet;
    a face mask positionable over the nose and mouth of a patient, having a hole formed therein for communication with said pump, and being arranged to seal against the patient's face in a substantially airtight manner; and
    a rigid conduit connected between said hole in said face mask and said air outlet of said inner cylindrical member.

2. A device as recited in claim 1, wherein
    an exhale aperture is formed in said rigid conduit substantially adjacent said mask to enable the patient to exhale air to an exterior of said device.

3. A device as recited in claim 2, further comprising
    a communication valve means for allowing air to pass from said pump to said mask through said rigid conduit during a pressurizing stroke, and for preventing air exhaled from the patient from flowing into said pump to cause the air exhaled from the patient to flow out through said exhale aperture during a non-pressurizing stroke.

4. A device as recited in claim 2, wherein
    said outer cylindrical member has a substantially closed distal end and a substantially open proximal end;

said inner cylindrical member has a substantially closed distal end and a proximal end which is substantially closed other than at said air outlet; and said valve means comprises at least one outer member aperture formed in said distal end of said outer cylindrical member, at least one valve provided at said at least one outer member aperture for regulating flow of air through said at least one outer member aperture by allowing ambient air to flow thereinto during a non-pressurizing stroke and preventing air flow from flowing therefrom during a pressurizing stroke, and at least one inner member aperture formed in said distal end of said inner cylindrical member.

5. A device as recited in claim 4, wherein
said at least one valve comprises at least one flap valve.

6. A device as recited in claim 1, wherein
said outer cylindrical member has a substantially closed distal end and a substantially open proximal end;

said inner cylindrical member has a substantially closed distal end and a proximal end which is substantially closed other than at said air outlet; and said valve means comprises at least one outer member aperture formed in said distal end of said outer cylindrical member, at least one valve provided at said at least one outer member aperture for regulating flow of air through said at least one outer member aperture by allowing ambient air to flow thereinto during a non-pressurizing stroke and preventing air flow from flowing therefrom during a pressurizing stroke, and at least one inner member aperture formed in said distal end of said inner cylindrical member.

7. A device as recited in claim 6, wherein
said at least one valve comprises at least one flap valve.

8. A device as recited in claim 1, wherein
said mask is substantially hollow and has a substantially triangular peripheral edge, said peripheral edge being substantially rounded.

9. A device as recited in claim 8, wherein
said mask is formed substantially of resilient plastic materials.

10. A device as recited in claim 1, wherein
said inner cylindrical member is formed of an opaque material; and said outer cylindrical member is formed of substantially transparent material, and has an axial marking provided thereon at a position in which, when a distal end of said inner cylindrical member is telescopically slid from a position substantially adjacent a distal end of said outer cylindrical member to a position aligned with said axial marking on said cylindrical outer member, a volume of air sufficient to resuscitate the patient is drawn into said pump.

* * * * *